(12) United States Patent
Birkner et al.

(10) Patent No.: US 11,717,156 B2
(45) Date of Patent: Aug. 8, 2023

(54) EYE TRACKING FIXATION MONITORING SYSTEMS AND METHODS

(71) Applicant: Alcon Inc., Fribourg (CH)

(72) Inventors: Sascha Birkner, Berlin (DE); Martin Gründig, Rangsdorf (DE)

(73) Assignee: Alcon Inc., Fribourg (CH)

( * ) Notice: Subject to any disclaimer, the term of this patent is extended or adjusted under 35 U.S.C. 154(b) by 415 days.

(21) Appl. No.: 16/991,937

(22) Filed: Aug. 12, 2020

(65) Prior Publication Data

US 2021/0045631 A1 Feb. 18, 2021

Related U.S. Application Data

(60) Provisional application No. 62/886,517, filed on Aug. 14, 2019.

(51) Int. Cl.
*A61B 3/113* (2006.01)
*G06T 7/73* (2017.01)
(Continued)

(52) U.S. Cl.
CPC ............ *A61B 3/113* (2013.01); *A61B 3/0025* (2013.01); *A61B 3/102* (2013.01); *A61B 3/1225* (2013.01);
(Continued)

(58) Field of Classification Search
CPC ....... A61B 3/113; A61B 3/0025; A61B 3/102; A61B 3/1225; A61B 3/14; A61B 3/18;
(Continued)

(56) References Cited

U.S. PATENT DOCUMENTS 10,761,602 B1 * 9/2020 Sharma .................. A61B 3/113
2003/0227611 A1 * 12/2003 Fein ...................... G02B 21/365
356/36

(Continued)

FOREIGN PATENT DOCUMENTS

DE 102018200829 A1 7/2019
WO 2015116981 A1 8/2015

OTHER PUBLICATIONS

Baluja et al., "Non-Intrusive Gaze Tracking Using Artificial Neural Networks." Jan. 5, 1994. XP055158923. pp. 1-14. Retrieved from http://www.dtic.mil/docs/citations/ADA275186 [retrieved on Dec. 21, 2020].

*Primary Examiner* — Mohammed A Hasan

(57) ABSTRACT

Systems and methods for tracking eye movement during a diagnostic procedure include an eye tracker capturing images of an eye, and a control processor configured to detect an eye position and orientation in each of the images, determine an eye fixation position and orientation relative to an optical axis of the eye tracker, estimate eye fixation parameters based at least in part on the determined eye fixation position and orientation, and track the eye position and orientation by analyzing the images to determine the eye position and orientation relative to the eye fixation parameters. The eye fixation parameters may comprise a reference position and orientation of the eye when fixated. A histogram is constructed of detected eye positions and orientations and analyzed to determine an eye fixation position and orientation.

18 Claims, 9 Drawing Sheets

(51) Int. Cl.
  *G06T 7/246*  (2017.01)
  *A61B 3/00*  (2006.01)
  *A61B 3/10*  (2006.01)
  *A61B 3/12*  (2006.01)
  *A61B 3/14*  (2006.01)
  *A61B 3/18*  (2006.01)
  *G06T 7/00*  (2017.01)
  *G06V 40/19*  (2022.01)

(52) U.S. Cl.
  CPC ............... *A61B 3/14* (2013.01); *A61B 3/18* (2013.01); *G06T 7/0016* (2013.01); *G06T 7/248* (2017.01); *G06T 7/74* (2017.01); *G06V 40/19* (2022.01); *G06T 2207/10101* (2013.01); *G06T 2207/30041* (2013.01)

(58) Field of Classification Search
  CPC ....... A61B 3/152; G06T 7/0016; G06T 7/248; G06T 7/74; G06T 2207/10101; G06T 2207/30041; G06V 40/19
  USPC .......................................................... 351/206
  See application file for complete search history.

(56) References Cited

U.S. PATENT DOCUMENTS

| | | | |
|---|---|---|---|
| 2005/0024586 A1* | 2/2005 | Teiwes | A61B 3/113 351/209 |
| 2009/0174865 A1 | 7/2009 | Siminou | |
| 2016/0249806 A1* | 9/2016 | Yates | A61B 3/125 351/207 |
| 2017/0280995 A1* | 10/2017 | Yates | A61B 3/14 |
| 2018/0084989 A1* | 3/2018 | Su | G06T 5/50 |

* cited by examiner

EYE TRACKING FIXATION MONITORING SYSTEMS AND METHODS

BACKGROUND

Field of the Disclosure

The present disclosure relates generally to eye tracking systems and methods, and more particularly, for example, to systems and methods for tracking the position and/or orientation of an eye in imaging, tracking, diagnostic and/or surgical systems.

Description of Related Art

A wide variety of ophthalmic devices are used to image, measure, diagnose, track, surgically correct and/or surgically repair a patient's eyes. The operation of an ophthalmic device such as a topography device, a keratometry device, a wavefront analyzer or another device that measures aspects of the eye (e.g., optically, geometrically, etc.), is often based on the assumption that the eye is maintained in a defined position and orientation with respect to the diagnostic device. The patient may be positioned by a human operator of the ophthalmic device and instructed, for example, to look into the device at a target object (e.g., a fixation light) to align the patient's line-of-sight (e.g., the axis along which a person looks at things) to an optical axis of the ophthalmic device. If the patient isn't properly fixating, readings may be inaccurate and/or the system may not be able to properly function.

To ensure accurate data acquisition, the human operator of the ophthalmic device is often tasked with monitoring the patient and/or monitoring feedback from the device during data acquisition to determine whether the patient has been properly fixating on a target object to align the eye. One known technique includes relying on the cooperation of the patient to fixate on a target object as instructed by a device operator. However, existing approaches have many drawbacks including human error in the patient's attempt to fixate (e.g., an elderly patient may be unable to maintain eye position, a patient may lack sufficient concentration to fixate the eye, the patient may not look directly at the target object, etc.) and human error by the operator monitoring the patient during the procedure. In another approach, retina scanning and imaging analysis may be used to track the patient's eye position and orientation, but operation of a retinal imaging system can interfere with a diagnostic procedure. As a result, retina scanning and imaging systems are often shut down or otherwise rendered inoperable for use in eye tracking during a diagnostic procedure performed using the ophthalmic device.

In view of the foregoing, there is a continued need in the art for improved techniques for determining and/or tracking the position and orientation of a patient's eye during an ophthalmic procedure.

SUMMARY

In accordance with various embodiments, systems and methods for evaluating and/or facilitating eye fixation are disclosed. The improvements disclosed herein may be used in various eye imaging, tracking, diagnostic and/or surgical systems to detect whether a patient is properly fixating during a measurement sequence, a surgical procedure and/or other procedures. In some embodiments, a system evaluates whether a patient is fixating on a certain optical axis of a diagnostic device. The system may use eye tracking techniques and a statistical evaluation in combination with a retina imaging system to allow for absolute fixation monitoring even in phases of the diagnostic procedure during which retina imaging is not available.

In various embodiments, a system includes an eye tracker configured to capture a first plurality of images of an eye, and a control processor configured to detect an eye position and orientation in each of the first plurality of images, determine an eye fixation position and orientation relative to an optical axis of the eye tracker, estimate eye fixation parameters based at least in part on the determined eye fixation position and orientation, and track the eye position and orientation by analyzing one or more images from the first plurality of images to determine the eye position and orientation relative to the eye fixation parameters. The eye fixation parameters may comprise a reference position and orientation of the eye when fixated.

In some embodiments, the control processor is further configured to detect the fixation position relative to the optical axis of the eye tracker by constructing and analyzing a histogram of detected eye positions and orientations. Analyzing the histogram may further include determining a relative maximum value and determining whether coordinates of the relative maximum value comprise a fixation position and orientation and determining whether coordinates of the relative maximum value may include a fixation position and orientation further comprise comparing the relative maximum value with a threshold and/or an average coordinate value of the histogram.

The system may further comprise a retina imaging system comprising an optical coherence tomography (OCT) scanner configured to perform a retinal scan that is configured to capture a second plurality of images of an eye, detect whether a fovea is present in one or more of the second plurality of images, identify a first image from the second plurality of images having the detected fovea, determine a second image from the first plurality of images having a temporal proximity to the first image, and analyze the second image to determine eye fixation parameters.

The control processor may also be configured to track the eye position and orientation and calculate an offset from the eye fixation parameters and determine if the offset is less than a threshold value. When the offset is less than the threshold value the eye is determined to be fixated and the control processor generates an indication of fixation. When the offset is greater than the threshold value the eye is determined to be out of alignment and the control processor generates an indication of no fixation.

In some embodiments, the control processor is further configured to perform an eye diagnostic procedure, and track eye position using the eye tracker during the eye diagnostic procedure. The system may further comprise a diagnostic device configured to perform an eye diagnostic procedure while tracking the position and orientation of the eye using an image capture device, which is further configured to receive data representative of fixation and eye position during the eye diagnostic procedure based, at least in part, on the data representative of fixation and eye position.

In various embodiments, a method includes capturing a first plurality of images of an eye, detecting an eye position and orientation in each of the first plurality of images, determining an eye fixation position and orientation relative to an optical axis of the eye tracker, estimating eye fixation parameters based at least in part on the determined eye fixation position and orientation, and tracking the eye position and orientation by analyzing one or more images from the first plurality of images to determine the eye position and orientation relative to the eye fixation parameters. The method may further include training a neural network to receive the first plurality of images and output a determination of an eye position. The eye fixation parameters comprise a reference position and orientation of the eye when fixated.

The method may further include detecting the fixation position relative to the optical axis of the eye tracker, by constructing and analyzing a histogram of detected eye positions and orientations, and analyzing the histogram further comprises determining a relative maximum value.

In some embodiments, the method includes performing a retina imaging scan of the eye using an optical coherence tomography (OCT) scanner, capturing a second plurality of images of an eye from the retina imaging scan, detecting whether a fovea is present in one or more of the second plurality of images, identifying a first image from the second plurality of images having the detected fovea, determining a second image from the first plurality of images having a temporal proximity to the first image, and analyzing the second image to determine eye fixation parameters.

In some embodiments, the method further includes tracking the eye position and orientation and calculating an offset from the eye fixation parameters and determine if the offset is less than a threshold value, wherein when the offset is less than the threshold value the eye is determined to be fixated and the control processor generates an indication of fixation, and wherein when the offset is greater than the threshold value the eye is determined to be out of alignment and the control processor generates an indication of no fixation.

The method may further comprise performing an eye diagnostic procedure, and tracking eye position using an eye tracker during the eye diagnostic procedure. The method may perform an eye diagnostic procedure while tracking the position and orientation of the eye using an image capture device, and modify the eye diagnostic procedure based, at least in part, on data representative of eye fixation parameters and a tracked eye position.

In various embodiments, a system comprises a retina imaging system configured to capture a first plurality of images of an eye, an eye tracker configured to capture a second plurality of images of the eye and analyze the captured images to track an eye position and orientation, and a control processor configured to detect the fovea in the first plurality of images, identify a first image from the first plurality of images having the detected fovea, determine a second image from the second plurality of images having a temporal proximity to the first image, and analyze the second image to determine eye fixation parameters.

The eye fixation parameters may comprise a reference position and orientation of the eye when fixated, and the control processor may be further configured to analyze the second plurality of images to determine a current eye position and orientation relative to the reference position and orientation of the eye when fixated. The control processor may be further configured to track the eye position and orientation and calculate an offset from the reference position and orientation. In some embodiments, when the offset is less than a threshold value, the eye may be determined to be fixated and the control processor generates an indication of fixation. If the offset is greater than the threshold value, the eye is determined to be out of alignment and the control processor generates an indication that the eye is not properly aligned.

In some embodiments, the retina imaging system comprises an optical coherence tomography (OCT) scanner configured to perform a retinal scan, and an ophthalmic device is provided for performing a diagnostic procedure. The retina imaging system may be inoperable to capture images of the eye and detect the fovea during a portion of the eye diagnostic procedure, and the control processor is configured to track an eye position using the eye tracker during the eye diagnostic procedure. An ophthalmic device may be configured to perform an eye diagnostic procedure while tracking the position and orientation of the eye using an image capture device. In some embodiments, the image capture device is configured to capture images of the surface of the eye without interfering with the diagnostic procedure. The ophthalmic device may be further configured to receive data representative of fixation and eye position during the eye diagnostic procedure based, at least in part, on the data representative of fixation and eye position. The eye tracking may be analyzed and updated during the diagnostic procedure.

The system may further include one or more neural networks trained to analyze the eye tracking data from the eye tracker, retina imaging data from a retina imaging system and/or data from the diagnostic procedure. The neural network may be trained using a dataset of labeled data comprising images and eye fixation and/or offset information. In some embodiments, a patient's retina imaging data and/or eye tracking data may be captured, analyzed and/or stored in one or more sessions and retrieved by the system for use during a diagnostic procedure.

In various embodiments, a method includes capturing, using a retina imaging system, a first plurality of images of an eye, and capturing, using an eye tracker, a second plurality of images of the eye. The method may further include detecting a fovea in the first plurality of images and tracking a position and orientation of the eye based on an analysis of the second plurality of images. The method may further include identifying a first image from the first plurality of images having the detected fovea, determining a second image from the second plurality of images having a temporal proximity to the first image, and analyzing the second image to determine eye fixation parameters. In some embodiments, the first plurality of images may be captured through an optical coherence tomography scan of the retina.

In some embodiments, the method is performed by an ophthalmic diagnostic device comprising the retina imaging system and the eye tracker. The eye fixation parameters may comprise a reference position and orientation of the eye when fixated, and the method may further include analyzing the second plurality of images to determine a current eye position and orientation relative to the reference position and orientation of the eye when fixated. The method may further comprise tracking a current eye position and orientation using the eye tracker and calculating an offset from the reference position and orientation and generating an indication of eye fixation when the offset is less than a threshold value.

The method may further include performing an eye diagnostic procedure, wherein the retina imaging system is inoperable to capture images of the eye and detect the fovea during at least a portion of the eye diagnostic procedure and tracking the eye position using the eye tracker during the eye diagnostic procedure. An eye diagnostic procedure may be performed while tracking the position and orientation of the eye using an image capture device, and the method may include receiving data representative of fixation and eye position during the eye diagnostic procedure based, at least in part, on the data representative of fixation and eye position. The eye tracking may be analyzed and updated during a diagnostic procedure.

The scope of the present disclosure is defined by the claims, which are incorporated into this section by reference. A more complete understanding will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Aspects of the disclosure and their advantages can be better understood with reference to the following drawings and the detailed description that follows. It should be appreciated that like reference numerals are used to identify like elements illustrated in one or more of the figures, where showings therein are for purposes of illustrating embodiments of the present disclosure and not for purposes of limiting the same. The components in the drawings are not necessarily to scale, emphasis instead being placed upon clearly illustrating the principles of the present disclosure.

DETAILED DESCRIPTION

Figure 1:
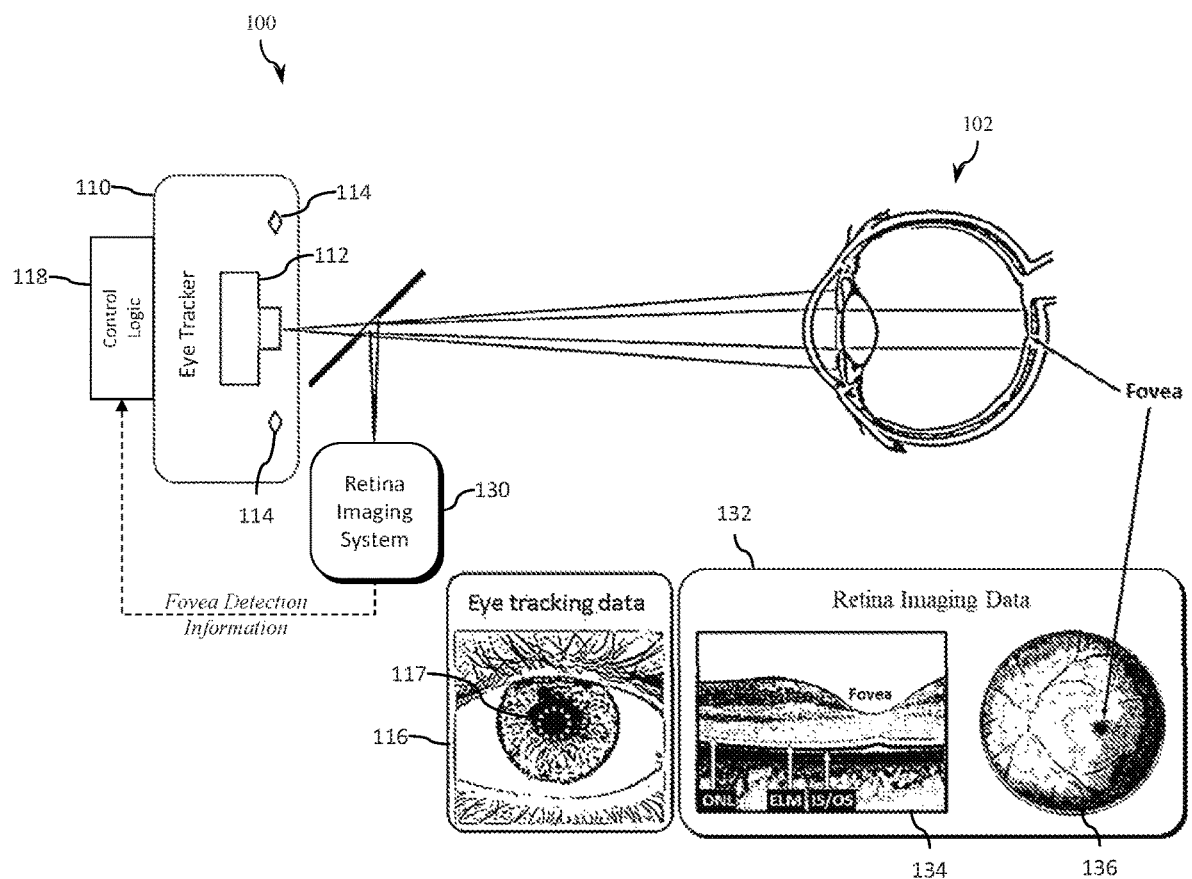
FIG. 1 illustrates an example eye tracking and imaging system, in accordance with one or more embodiments of the present disclosure.

Systems and methods are disclosed herein for evaluating and/or facilitating eye fixation in an eye imaging, tracking, diagnostic and/or surgical system. For example, the improvements disclosed herein may be used to assist a device operator in aligning the patient's line-of-sight to an optical axis of an ophthalmic device prior to activating an ophthalmic device to perform a measurement sequence or other diagnostic procedure.

In accordance with various embodiments, accurate measurement of a patient's eye is facilitated using a diagnostic system that determines whether the patient's line-of-sight (also referred to herein as the patient's visual axis) is in alignment with an optical axis of the diagnostic system. The patient's line-of-sight/visual axis may be the axis along which the patient's eye is oriented to look at an object. The diagnostic data acquired in accordance with the systems and methods disclosed herein is more meaningful and accurate than data acquired through conventional approaches. The systems and methods may also be configured to provide feedback to a human operator of the diagnostic device on whether the patient has been fixating on the proper axis during data acquisition.

The systems and methods disclosed herein provide numerous advantages over conventional approaches. For example, data acquisition from a patient's eye may include instructing a patient to fixate on a target object to properly align the eye. However, this technique is prone to error because the human operator of the diagnostic device is often relying on the cooperation of the patient who may not be properly fixating on the target object. In another approach, retina optical coherence tomography (OCT) may be used to image the patient's retina and provide an indication to the operator of whether the patient is properly fixating. However, the analysis of the OCT scan is only valid while the OCT is scanning the retina. If the diagnostic system uses a different type of sensor during a procedure which requires switching the OCT scan to a different section of the eye or switching the OCT scan off (e.g., for eye safety reasons), then the analysis will not be reliable for these periods of the measurement. Other optical retina imaging techniques suffer the same drawbacks as the retina-OCT scan. In a measurement sequence that utilizes different sensors, the fixation information is only valid for a period in which the retina imaging is operational. During periods in which the retina imaging needs to be switched off, fixation information is unavailable.

The systems and methods disclosed herein overcome the aforementioned limitations and other limitations with conventional systems and introduce numerous advantages. The present disclosure provides improved cost-efficient solutions that may be implemented in variety of systems, including conventional ophthalmic diagnostic devices that use a camera and an illumination system. The combination an ophthalmic diagnostic device with a retina OCT system allows for absolute fixation control even when the retina OCT is switched off. In some embodiments, a system and method will provide accurate fixation information after the retina OCT has detected the fovea at least once during a measurement sequence. In other embodiments, a system and method will provide accurate fixation information in implementations where a retina OCT scan is not available and/or the fovea has not been detected.

Embodiments of the present disclosure will now be described in further detail with reference to the figures. Referring to FIG. 1, a system 100 in accordance with one or more embodiments includes an eye tracking module 110 (also referred to herein as an "eye tracker") and a retina imaging system 130, which are communicably coupled. The eye tracking module 110 is configured to track the orientation of an eye 102 and may include an imaging device 112 and one or more illumination components 114. In some embodiments, the imaging device 112 is a digital camera or other digital imaging device configured to image certain features of the eye such as the pupil and corneal limbus (the border between the cornea and the white of the eye, i.e., the sclera) and reflections from the illumination components 114. In some embodiments, for example, the illumination components 114 may comprise an LED ring positioned around the camera optics (e.g., coaxial illumination around the imaging device) such that the center of the ring resembles the center of curvature of the cornea.

The system 100 includes control logic 118, which may include a processor executing stored program instructions configured to perform the functions disclosed herein. In some embodiments, the control logic 118 performs a measurement sequence with a plurality of images captured by the imaging device 112. The measurement sequence determines the position and orientation of the eye 102 by using the position of detectable features of the eye 102 in the image data (such as eye tracking data 116), such as the pupil, limbus, and iris features. The measurement sequence may also determine the position of the reflection of the illumination system at the cornea (such as the reflections 117 comprising a circle pattern of illuminated elements). In some embodiments, during the measurement sequence, the position and orientation of the eye 102 is continually determined using the captured images.

The control logic 118 may be embodied in the eye tracker 110, the retina imaging system 130 and/or in other system components. The control logic 118 is configured to detect relative eye movement during operation of the system 110, which may include detecting and tracking eye features (e.g., detect the pupil) from the captured images and knowledge of the illumination source position. For example, detecting and calculating an offset of the center of the pupil and an offset of the cornea curvature may provide information about the relative gaze of the eye.

The retina imaging system 130 may include any device or system for imaging the retina of the eye 102. The retina imaging system 130 may be implemented as a retina optical coherence tomography (OCT) system, a retina optical system, or similar system for imaging the retina. In some embodiments, the retina imaging system 130 and/or the control logic 118 is configured to detect the fovea of the patient at least once during the full measurement sequence. As a result, the retina imaging system 130 does not need to be active during the full diagnostic sequence (e.g., for technical or safety reasons) and may be shut down or paused as desired.

The fovea often appears as depression in the retina which may be detected in certain retina imaging systems. In various embodiments, the retina imaging system 130 generates retina imaging data 132, such as a retina OCT image 134 and/or a fundus image 136. The retina imaging system 130 may comprise retina OCT scanning system, a fundus imaging system, or other similar device. If the patient is fixating on a target object associated with the system 100, the fovea will be present in the center of the optical axis of the retinal imaging device. The retina imaging device may only need to scan the center part around the optical axis of the device. If the patient is fixating, then the fovea will be present in the retina imaging data. In some embodiments, the retina imaging device is configured to image the back of the eye for fovea detection. If the system needs to image a different part of the eye (e.g., high resolution scan of the cornea), then the fovea will not be visible in the image and the eye tracker 110 will be used to track the eye position and rotation.

The system 100 coordinates the processing of information relating to the orientation of the eye from the eye tracking module 110 (such as eye tracking data 116, including detected illumination source reflections 117) with the information from the retina imaging system 130 (such as retina imaging data 132). In operation, if the system 100 (e.g., via the retina imaging system 130 and/or control logic 118) detects the fovea in a certain area of the retina imaging data 132, then the corresponding orientation of the eye is known to the system 100. With this information, the system 100 may further determine if the patient is fixating correctly even in phases of the measurement in which retina imaging is not available.

In some embodiments, if the patient is fixating, the fovea will appear in the center of the image. The eye tracking module 110 is configured to image and the track eye position and eye rotation at the same time as the retinal imaging. In some embodiments, the captured images include associated temporal characteristics such as a timestamp, frame reference (e.g., 10 frames ago), or other information allowing synchronization of the retinal images and the eye tracker information. After the fovea is detected, the fovea detection information, which may include a corresponding temporal characteristic and an indication of whether the fovea was detected may be provided to control logic 118, eye tracking module 110, and/or other system components.

In some embodiments, the analysis of the position and orientation of the eye 102 includes a method that compares the orientation/position of the eye at the time the fovea was visible with the retina imaging system with current eye tracking data. The system 100 may be used, for example, in a diagnostic procedure that includes a measurement sequence. By tracking the eye position and orientation during a procedure using the eye tracker 110, measurement data may be gathered and analyzed with the corresponding eye tracking data. In one embodiment, measurement data acquired when the eye 102 was fixated (e.g., when the eye position is within an acceptable offset from a fixation position) is considered valid and used for further diagnostics/analysis and measurement data acquired when the eye 102 was not fixated (e.g., when the eye position is outside an acceptable offset from a fixation position) may be ignored and/or discarded.

In various embodiments, the system 100 uses the fovea detection information to establish reference fixation information, which may include a certain orientation of the pupil in relation to the cornea. The eye tracker 110 can receive fovea detection information (e.g., fixation determined at particular time or other temporal reference), retrieve one or more corresponding images from the same timeframe, and analyze the captured image(s) to determine the specific relationship between the pupil and the cornea center during fixation. The eye position may then be tracked by comparing the eye position and orientation in newly captured images with the eye position and orientation from reference images. This allows the retina imaging system 130 to image another part of the eye 102 (or operation of other ophthalmic equipment as desired) while the eye tracker 110 confirms that the eye is fixating. The eye tracking module 110 may provide fixation information to the retina imaging system 130 indicating whether a current scan was taken while the eye was fixating (within a range of error relative to the reference data) or whether the current scan was taken while the was not fixating, such as when the offset between the current eye position and the reference eye position exceeds a threshold value.

Figure 2:
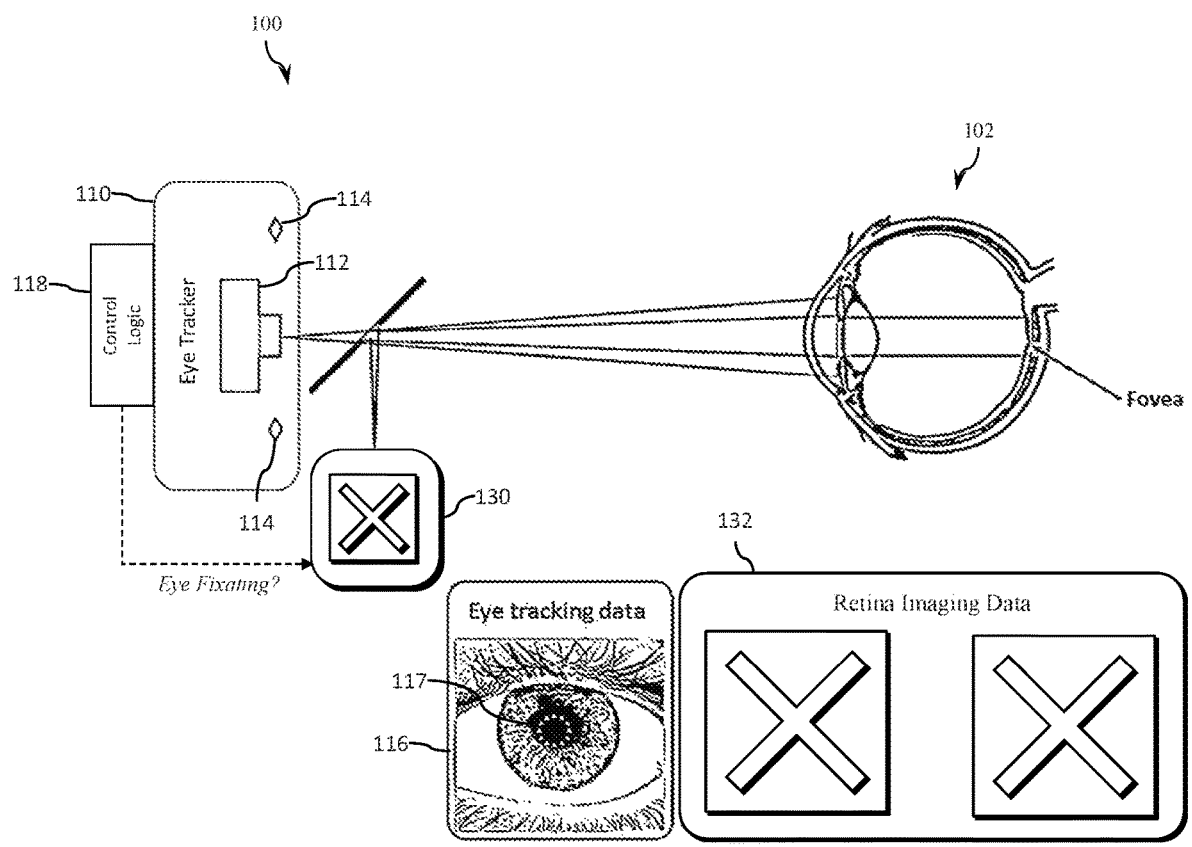
FIG. 2 illustrates the example eye tracking and imaging system of FIG. 1 during a diagnostic procedure, in accordance with one or more embodiments of the present disclosure.

Referring to FIG. 2, during operation of the system 100 the retina imaging system 130 may be shut down during a diagnostic or other procedure such that retina imaging data 132 is no longer generated. If the fovea has been previously detected by the retina imaging system 130 at least one time as described with reference to FIG. 1, the system 100 can continue to provide the device operator information about the patient's eye fixation, even during phases of the procedure in which no retina imaging is available. For example, the system 100 may compare the current eye position and orientation captured using the eye tracker 110 to the eye position and orientation determined when the retina imaging system 130 detected the fovea. The eye tracker 110 may provide an indication to the device operator through one or more visual (e.g., indicator light, status information on a display screen) or audible cues (e.g., beeps). The eye tracker 110 may further provide fixation information to other components of the system 100, for example, to control operations that require eye fixation and/or to validate/invalidate acquired data.

It will be appreciated that the system and methods described in FIGS. 1 and 2 are example implementations of various embodiments, and the teachings of the present disclosure may be used in other eye tracking systems, such as systems or devices using an illumination system generating purkinje reflections and a camera to capture digital images of the eye.

To aid in determining whether the eye is fixated, the control logic 118 may be configured to determine a current position and orientation of the eye and calculate an offset to determine whether the eye is sufficiently fixated on the desired object. In one embodiment, a threshold may be determined and any offset lower than the threshold will result in a determination that the eye is fixated. In some embodiments, the fixation determination and threshold are application dependent and different offsets may be acceptable for difference implementations.

In an example operation, the retina imaging system 130 may be configured to perform a plurality of scans and retina imaging analysis, which may be focused on various parts of the eye 102. In one configuration, the retina imaging system 130 is configured to image the back of the eye and identify the fovea. The fovea is likely to appear in the middle of the image, indicating that the patient's gaze is aligned with the optical axis of the system 100. The retina imaging system 130 may be configured to next perform other scans of different parts of the eye, from which fovea detection is not available. It is desirable for the patient to fixate on the target object during these scans, but the retina imaging system may be unable to detect the fovea to confirm proper eye position and alignment.

In some embodiments, the retina imaging system 130 identifies a timeframe (e.g., a period of time, one or more images, a sequential index value, etc.) in which the fovea was detected, allowing the eye tracker to identify corresponding eye tracking imagery that was taken at the same, or approximately the same time. The eye tracking module 110 may then determine a reference position of the eye associated with the fixation position, including relative position of the pupil and cornea. The eye fixation information may be immediately used by the system 100 to track the eye position and orientation and/or stored and retrieved for use by the system 100 at a later time. For example, eye fixation information may be determined and stored for a patient and retrieved for use by the system 100 (or similar system) for subsequent procedures for the patient or for offline analysis of captured images.

While the retina imaging device 130 is performing other scans and/or other ophthalmic components are in operation, the eye tracker 110 captures a stream of images and analyzes the eye position and alignment with reference to the position and orientation determined from the reference image(s). This analysis may be performed in real time during a procedure and/or offline (e.g., when analyzing previously captured data). The current images are compared to the reference image(s) and an offset is calculated. If the offset is less than a threshold then the eye is fixating and the corresponding retina images are accurate. If the offset is greater than the threshold then the eye is not fixating and the corresponding retina images may be flagged, discarded or other action taken.

In some embodiments, the eye tracker 110 continually images the eye throughout the procedure. For each frame, the pupil position may be detected in the image based, at least in part, on where reflections are detected in the image stream. In various embodiments, the information tracked and recorded may include one or more of the image, image features extracted from the image, image properties, pupil location and/or reflection position in the image. The eye tracking system and retina imaging system are synchronized such that for each retina scanned image, one or more corresponding eye tracker images may be identified. In one embodiment, there is a one-to-one correspondence. In other embodiments, the images are synchronized through a timestamp or other synchronization data associated with the captured images.

It will be appreciated that while the eye tracking module 110 and retina imaging system 130 are described as separate components, the system 100 may comprise a diagnostic device with various subcomponents including the eye tracking module 110, the retina imaging system 130 and other subcomponents. In some embodiments, a central processor may be provided to control the operation of the system 100, synchronize and control communications between the two systems and perform other system functions. Analysis of the eye position and orientation may be performed in real-time by the system 100, or later after the procedure is complete. Online, the system 100 may provide feedback to the patient and operator. Offline, the system 100 and/or other systems may perform more a complex analysis to achieve more accurate scans and results.

In some embodiments, the system 100 may comprise a larger diagnostic device that includes a camera (e.g., for imaging the surface of the eye), and a second component for measuring the retina. The system 100 may include a plurality of sensors configured to image the eye to create a 3-D eye model. A first sensor may include a camera(s) to recover the cornea shape and do the eye tracking. A second sensor may include a wavefront sensor that measures the wavefront of the eye (optical parameters of the eye). A third sensor may include an OCT system that can measure distances between different refractive surfaces of the eye. The OCT may include multiple modes and resolutions including a full eye mode, half-eye mode (front of eye) and cornea mode (having higher resolution).

Figure 4:
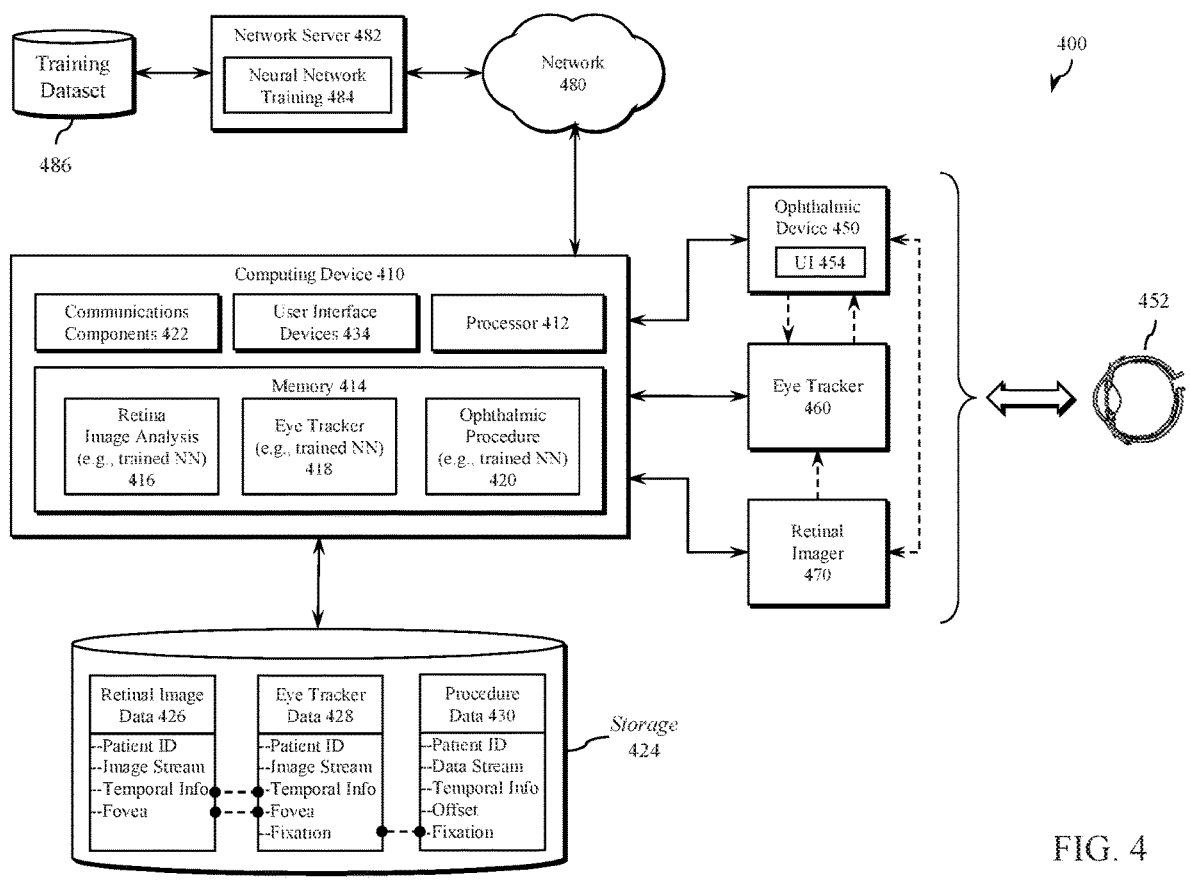
FIG. 4 illustrates an example computing system, in accordance with one or more embodiments of the present disclosure.

Sensor data may be provided to a processor (e.g., as illustrated in FIG. 4) which collects and stores the data in a memory. The processor may use a fusion algorithm to derive a 3D model of the eye comprising a parameterized model that incorporates the various sensor data. The 3D model may be used, for example, for cataracts and corneal refractive surgery planning. The data may be used for ray tracing, to assist in intraocular lens (IOL) implant placement in the eye, etc. The fovea detection and eye tracking innovations described herein may be used with any diagnostic device or instrument that includes a device that scans through the retina. Eye tracking may be implemented in a keratometer, biometer, wavefront measurement device, and other devices including a digital camera and illumination.

In various embodiments, the absolute eye orientation utilizes a device that scans through the retina, such as an OCT device, which may include biometers and other devices that (i) provide retina scanning and other diagnostic modes, and (ii) other sensors that perform other input functions. The system disclosed herein may be used with more components, different components, and fewer diagnostic devices in various embodiments.

Advantages of the present application will be understood by those skilled in the art. The systems and methods disclosed herein provide information regarding the times when the patient is fixating and not fixating, independent of the patient (e.g., not relying on the patient's cooperation). The eye tracking information is collected and provided to a processor, which enables further analysis. Other sensor data may be acquired and validated by backtracking through the data to adjust for a known or projected orientation based on the eye tracking data. For example, an eye position may be determined and provided to the retina imaging system for use in analyzing the scan data. The ability to flag whether the patient is fixation or not fixating is valuable for many system operations. The ability to determine a degree of fixation allows the system to adapt for use in variety of implementations. Storing the captured data for later retrieval and analysis allows for further calculations offline and more complex analysis and options, such as through use of complex neural networks or other analytical processes.

In one embodiment, the processor is configured with a reference point and a threshold which are used to filter out unreliable sensor data. For example, the system may be configured such that a small gaze change (e.g., 0.03 degrees of offset) may be okay, but a larger gaze change will indicate unreliable data that should be filtered out. In some embodiments, the sensor data acquired during fixation may be averaged together or otherwise combined. In other embodiments, the acquired data may be analyzed along with eye position and orientation information by calculating an eye position during acquisition using a calculated offset and known eye position and orientation at a reference point. In some embodiments, the various sensor and data inputs and calculations may be processed using a fusion engine to generate desired output data.

Figure 3:
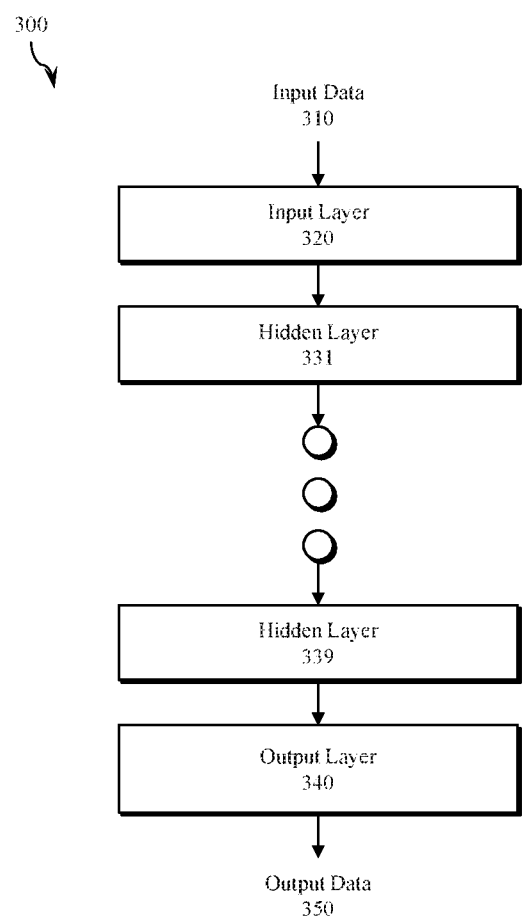
FIG. 3 illustrates an example neural network, in accordance with one or more embodiments of the present disclosure.

In various embodiments, one or more neural networks may be used for image and data analysis, such as to determine whether the eye is fixated on a target object. FIG. 3 is a diagram of an example multi-layer neural network 300 according to some embodiments. The neural network 300 may be representative of a neural network used to implement at least some of the logic, image analysis and/or eye fixation determination logic as described herein. The neural network 300 processes input data 310 using an input layer 320. In some examples, input data 310 may correspond to image capture data and captured retina image data as previously described herein. In some embodiments, the input data corresponds to input training data used to train neural network 300 to make fixation, orientation and/or other determinations.

Input layer 320 includes a plurality of neurons that are used to condition input data 310 by scaling, range limiting, and/or the like. Each of the neurons in input layer 320 generates an output that is fed to the inputs of a hidden layer 331. Hidden layer 331 includes a plurality of neurons that process the outputs from input layer 320. In some examples, each of the neurons in hidden layer 331 generates an output that collectively are then propagated through one or more additional hidden layers that end with hidden layer 339, as illustrated. Hidden layer 339 includes a plurality of neurons that process the outputs from the previous hidden layer. The outputs of hidden layer 339 are fed to an output layer 340. Output layer 340 includes one or more neurons that are used to condition the output from hidden layer 339 by scaling, range limiting, and/or the like. It should be understood that the architecture of neural network 300 is representative only and that other architectures are possible, including a neural network with only one hidden layer, a neural network without an input layer and/or output layer, a neural network with recurrent layers, and/or the like.

In some examples, each of input layer 320, hidden layers 331-339, and/or output layer 340 includes one or more neurons. In some examples, each of input layer 320, hidden layers 331-339, and/or output layer 340 may include a same number or a different number of neurons. In some examples, each of the neurons takes a combination (e.g., a weighted sum using a trainable weighting matrix W) of its inputs x, adds an optional trainable bias b, and applies an activation function $f$ to generate an output a as shown in the equation $a=f(Wx+b)$. In some examples, the activation function $f$ may be a linear activation function, an activation function with upper and/or lower limits, a log-sigmoid function, a hyperbolic tangent function, a rectified linear unit function, and/or the like. In some examples, each of the neurons may have a same or a different activation function.

In some examples, neural network 300 may be trained using supervised learning where combinations of training data that include a combination of input data and a ground truth (e.g., expected) output data. Differences between the generated output data 350 and the ground truth output data may be fed back into neural network 300 to make corrections to the various trainable weights and biases. In some examples, the differences may be fed back using a back-propagation technique using a stochastic gradient descent algorithm, and/or the like. In some examples, a large set of training data combinations may be presented to neural network 300 multiple times until an overall loss function (e.g., a mean-squared error based on the differences of each training combination) converges to an acceptable level. The trained neural network may be stored and implemented in an ophthalmic device (e.g., system 100 of FIG. 1) for real time classification of captured images (e.g., as fixated or not fixated), and/or stored and implemented in an offline system for analysis of the captured data.

FIG. 4 illustrates an example computing system that may include one or more components and/or devices of system 100, including an implementation of an eye tracking module 110 and a retina imaging system 130. The computing system 400 may include one or more devices in electrical communication with each other, including a computing device 410 that includes a processor 412, a memory 414, communications components 422 and a user interface 434.

The processor 412 may be coupled to various system components via a bus or other hardware arrangement (e.g., one or more chipsets). The memory 414 may include a read only memory (ROM), a random-access memory (RAM), and/or other types of memory (e.g., PROM, EPROM, FLASH-EPROM, and/or any other memory chip or cartridge). The memory 414 may further include a cache of high-speed memory connected directly with, in close proximity to, or integrated as part of processor 412. The computing device 410 may access data stored in ROM, RAM, and/or one or more storage devices 424 through a cache for high-speed access by the processor 412.

In some examples, memory 414 and/or storage device 424 may store one or more software modules (e.g., software modules 416, 418, and/or 420), which may control and/or be configured to control processor 412 to perform various actions. Although the computing device 410 is shown with only one processor 412, it is understood that processor 412 may be representative of one or more central processing units (CPUs), multi-core processors, microprocessors, microcontrollers, digital signal processors (DSPs), field programmable gate arrays (FPGAs), application specific integrated circuits (ASICs), graphics processing units (GPUs), tensor processing units (TPUs), and/or the like. In some examples, computing device 410 may be implemented as a stand-alone subsystem and/or as a board added to a computing device or as a virtual machine.

To enable user interaction with system 400, the computing device 410 includes one or more communication components 422 and/or one or more user interface devices 434 facilitating user input/output (I/O). In some examples, the one or more communication components 422 may include one or more network interfaces, network interface cards, and/or the like to provide communication according to one or more network and/or communication bus standards. In some examples, the one or more communication components 422 may include interfaces for communicating with computing device 410 via a network 480, such as a local area network, a wireless network, the Internet or other network. In some examples, the one or more user interface devices 434 may include on or more user interface devices such as keyboards, pointing/selection devices (e.g., mice, touch pads, scroll wheels, track balls, touch screens), audio devices (e.g., microphones and/or speakers), sensors, actuators, display devices, and/or other input/output devices.

According to some embodiments, the user interface devices 434 may provide a graphical user interface (GUI) suitable for aiding a user (e.g., a surgeon and/or other medical personnel) in the performance of the processes disclosed herein. The GUI may include instructions regarding the next actions to be performed, diagrams of annotated and/or un-annotated anatomy, such as pre-operative and/or post-operative images of an eye, requests for input, and/or the like. In some examples, the GUI may display true-color and/or false-color images of the anatomy, and/or the like.

The storage device 424 may include non-transitory and non-volatile storage such as that provided by a hard disk, an optical medium, a solid-state drive, and/or the like. In some examples, the storage device 424 may be co-located with computing device 410 (e.g., a local storage device) and/or remote from system 400 (e.g., a cloud storage device).

The computing device 410 may be coupled to one or more diagnostic, imaging, surgical and/or other devices for use by medical personnel. In the illustrated embodiment, the system 400 includes an ophthalmic device 450, an eye tracker 460 and a retinal imager 470, which may be embodied in one or more computing systems, including computing device 410. The ophthalmic device 450 includes a user interface 454 for controlling and/or providing feedback to an operator conducting a procedure on a patient's eye 452. The ophthalmic device 450 may include devices for imaging, measuring, diagnosing, tracking, and/or surgically correcting and/or repairing the patient's eye 424.

The ophthalmic device 450 is communicable coupled to the eye tracker 460 (such as eye tracker 110 of FIG. 1), which receives eye imaging data from the ophthalmic device, and provides status information of the position and alignment of the eye 452 during a procedure. The retinal imager 470 is communicably coupled to both the ophthalmic device 450 and the eye tracker 460 and configured to capture a retinal image of the eye 452 for use in an ophthalmic procedure and for detection of the fovea for use in fixation tracking.

In various embodiments, the memory 414 includes a retina imaging analysis module 416, an eye tracker module 418, and an ophthalmic procedure module 420. The retina imagine analysis module 416 includes program instructions for instructing the processor 412 to capture retina images using the retina imager 470 and/or analyze captured retina images. The retina image analysis module 416 may include a neural network trained to receive one more captured retina images (e.g., a captured image, a real-time stream of retinal images, stored retina images, etc.), extract relevant image features, and detect the presence or absence of the fovea (e.g., output a classification indicting fovea detection, output a probability of proper eye position and/or alignment, etc.).

The eye tracker module 418 includes program instructions for instructing the processor 412 to capture images of the eye 452 using the eye tracker 460 and/or analyze captured images. The eye tracker module 418 may include a neural network trained to receive one or more captured images (e.g., a captured image, a real-time stream of eye images from eye tracker 460, stored eye images, etc.), extract relevant images features, and output eye tracking information (e.g., output an indication of eye alignment, output a probability of proper eye position and/or alignment, output an offset of the eye from a proper position and alignment, etc.).

In various embodiments, the eye tracker 418 is configured to determine a reference eye position based on alignment data received from the retina image analysis module 416. For example, the eye tracker 418 may receive fovea detection information from the retina image analysis module 416, which is used to identify corresponding images from the eye tracker 460 that show the eye 452 in proper alignment. The eye tracker module 418 is further configured to analyze images captured by the eye tracker 460 and output eye tracking information with reference to the reference image.

The ophthalmic procedure 420 includes program instructions for instructing the processor 412 to conduct an ophthalmic procedure and may include user input and output during the procedure through user interface 454, and analysis of captured data. In some embodiments, the ophthalmic procedure 420 includes a trained neural network for analyzing data captured during the procedure. The ophthalmic procedure 420 receives eye tracking information from the eye tracker module 418, which may include an alignment status within an acceptable offset threshold, offset data, and/or other information. In some embodiments, the ophthalmic procedure 420 is configured to operate when the patient's eye 452 is in an acceptable alignment position and provide an indication (e.g. a sound such as a beep, a visual indication such as a flashing light, etc.) through the user interface 454 to an operator of the ophthalmic device 450 when the patient's eye is out of alignment.

The system 400 may store captured retinal, eye tracking and ophthalmic procedure data for later processing, including online processing (e.g., during subsequent procedure) and offline processing. The storage 424 may store retinal images data 426 captured for a patient, which may include a patient identifier, a stream of captured images, temporal information (e.g., a time stamp, sequential index, etc.) and/or information on whether the fovea was detected in an image. The storage 424 may also store eye tracker data 428, which may include a patient identifier, a stream of captured images, temporal information (e.g., a time stamps, sequential index, etc.), whether the captured image corresponds with a time period during which the fovea was detected, and/or fixation information providing a reference position of an eye during fixation. The storage 424 may also store procedure data 430 captured for a patient during the procedure, including a patient identifier, a stream of data captured during the procedure (e.g., images, data readings, data calculations, etc.), temporal information (e.g., a time stamp, sequential index, etc.), offset information calculated for the eye position at a point in the procedure, and/or whether the eye was fixated at a time during the procedure.

The computing device 410 may communicate with one or more network servers 482 providing one or more application services to the computing device. In some embodiments, the network server 482 includes a neural network training module 484 for training one or more of the neural networks using a training dataset 486, which may include labeled images. For example, the retina image analysis module 416 may include a neural network trained using a set of retina images labeled to identify the presence and/or absence of the fovea. The eye tracker module 418 may include a neural network trained using a set of captured eye images labeled to identify the presence and/or absence of the fovea. The eye tracker module 418 may further include a neural network trained using a set of captured eye images and reference data, labeled to identify an offset of the image with respect to the reference data. The ophthalmic procedure 420 may include a neural network trained using a set of data representing data captured during a procedure, including alignment and/or offset data from the eye tracker module 418.

Figure 5:
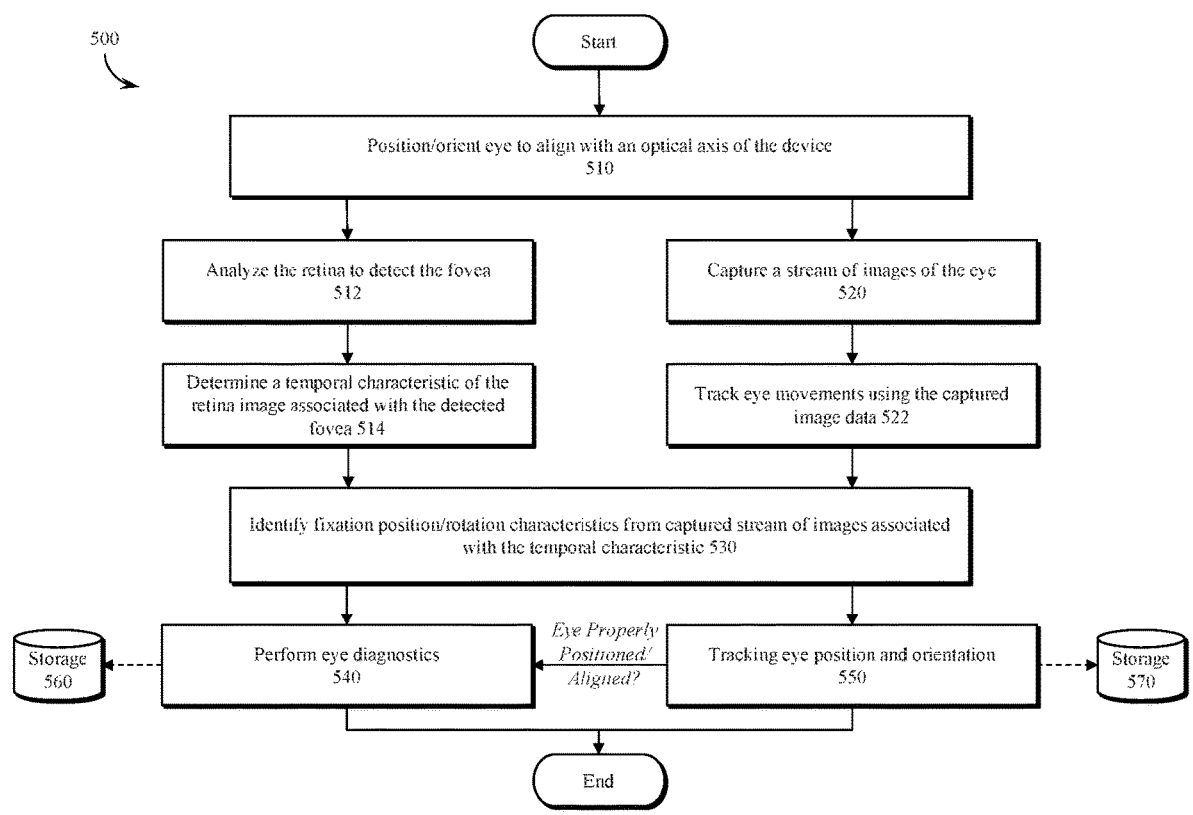
FIG. 5 illustrates an example operation of an ophthalmic system, in accordance with one or more embodiments of the present disclosure.

Referring to FIG. 5, an embodiment of a method 500 for operating the system 100 of FIG. 1 will now be described. In step 510, the patient is positioned at the ophthalmic system and directed to focus on a target object to align the patient's line of sight with an axis of alignment of the ophthalmic device. In step 512, the retina is analyzed to detect the fovea. In one embodiment, the ophthalmic system includes a retina imaging system (such as retina imaging system 130 of FIG. 1) configured to scan the retina, acquire scanned retina data, and analyze the acquired data to detect the fovea. In some embodiments, the fovea is visible in the center of the OCT image if the eye is fixating. In step 514, a temporal characteristic of the retina image data associated with the detected fovea is determined. In various embodiments, the temporal characteristic may include a timestamp, a sequential image index, or other criteria allowing synchronization of the retina imaging data to other components of the system.

Simultaneously, an eye tracking system captures a stream of images of the eye in step 520 and tracks the eye movement using the captured image data in step 522. In some embodiments, while detecting the retina in steps 512 and 514, the eye tracking system tracks eye motion and determines a fixation location and applies acceptable offsets for a given procedure. In step 530, the captured image or images matching the temporal characteristic are identified and analyzed to determine a position and orientation of the eye when fixated on the target object. In step 540, system diagnostics are performed, which may include eye measurements and other acquired data. In some embodiments, the analysis of the retina (step 512) and determination of temporal characteristics associated with the detected fovea (step 514) are performed by a retina imaging system, which is disabled during the eye diagnostics of step 540. Thus, the retina imaging system is not available to track the eye position during the diagnostic procedure.

During the measurement in step 540, the eye tracking system tracks the position and orientation of the eye in step 550 to determine whether the eye is properly positioned and aligned during measurement. In some embodiments, the eye tracking system focuses on the front side of the cornea or inside of the chamber. The eye tracking system may analyze captured images of the eye during the diagnostics (step 540) and determines a current position and rotation based on the captured images. The current position and rotation is compared with the fixation position and rotation to determine an offset. If the offset is below an error threshold, then the eye is determined to be in proper position and alignment for measurement. If the offset is above an error threshold, then the diagnostic process and/or the system operator may be notified that the eye is out of alignment allowing the operator to pause the diagnostic procedure and instruct the patient to reposition the eye, allowing for the associated measurement data to be determined valid/invalid, or allowing for other actions to be taken. In some embodiments, the data acquired during the eye diagnostic procedure (step 540) is stored in a storage device 560 and the data acquired during the eye tracking procedure (step 550) is stored in a storage device 570, for subsequent processing and analysis. In one embodiment, the patient's data is tracked in addition to the fovea information and may be verified using fovea information where available. In this manner, a range of values and an average fixation position may be determined.

The retina imaging information and/or fovea detection information may not always be available for use in eye tracking. Some ophthalmic devices, for example, do not include an OCT retina scanner. In some procedures, the fovea may not have been reliably detected before the start of the procedure (e.g., the patient wasn't properly fixating, the fovea wasn't detected in the image with a satisfactory degree of certainty, operator or system error, etc.). In these embodiments, the absolute fixation position may be determined based at least in part on an analysis of images captured from the eye tracker (e.g., images of the surface of the eye).

In various embodiments, a fixation analysis is performed by detecting eye positions in a stream of images captured from a camera and analyzing the results to estimate an absolute fixation position. The analysis may include a statistical analysis using a histogram of eye positions determined from the captured images. If the histogram shows a clear maximum according to the analysis, then the method can estimate the absolute fixation position. If the histogram shows no clear maximum, then the method may indicate that no fixation has been detected. In some embodiments, the analysis of the captured images may include a comparison between the patient's eye and other eyes in known positions (e.g., use of a neural network trained using a set of labeled training images), historical fixation information for the patient, image analysis (including tolerances/thresholds), and/or other analysis of available information. In some embodiments, the method may rely on the operator and patient to properly fixate the patient's eye. In some embodiments, the method may address scenarios in which the operator and/or patient error causes the images to not reflect fixation (e.g., if the patient fixates intentionally on a wrong spot, or the operator doesn't properly instruct and/or monitor the patient).

Embodiments of systems and methods for eye tracking in which a retina OCT scan is not available and/or the fovea has not been reliably detected before the procedure will now be described with reference to FIGS. 6-9. As previously discussed, an accurate measurement of the eye using an ophthalmic device usually starts with an alignment of the patient's line-of-sight (the patient's visual axis) to a certain optical axis of the ophthalmic device. The line-of-sight in this context may be the axis along which the patient looks at things. The resulting diagnostic data and/or other results of the ophthalmic procedure may be unreliable during the periods in which the patient was not properly fixating. Systems and methods are disclosed herein that enable an ophthalmic device to estimate the absolute fixation position from an analysis of images captured by an eye tracker module (e.g., eye tracker 110 of FIG. 1 and/or other another image capture device).

The estimated eye fixation information may be used by the ophthalmic device to provide feedback to a device operator regarding whether the patient is fixating (or not properly fixating) on a certain optical axis of a diagnostic device during a procedure (e.g., a measurement procedure). The ophthalmic device may use the estimated eye fixation information during the procedure to identify periods during which the patient is properly fixating. The system may also use the estimate eye fixation information to determine whether data acquired during a procedure is reliable and/or unreliable data based at least in part on whether the patient was determined to be fixating during data acquisition.

Figure 6:
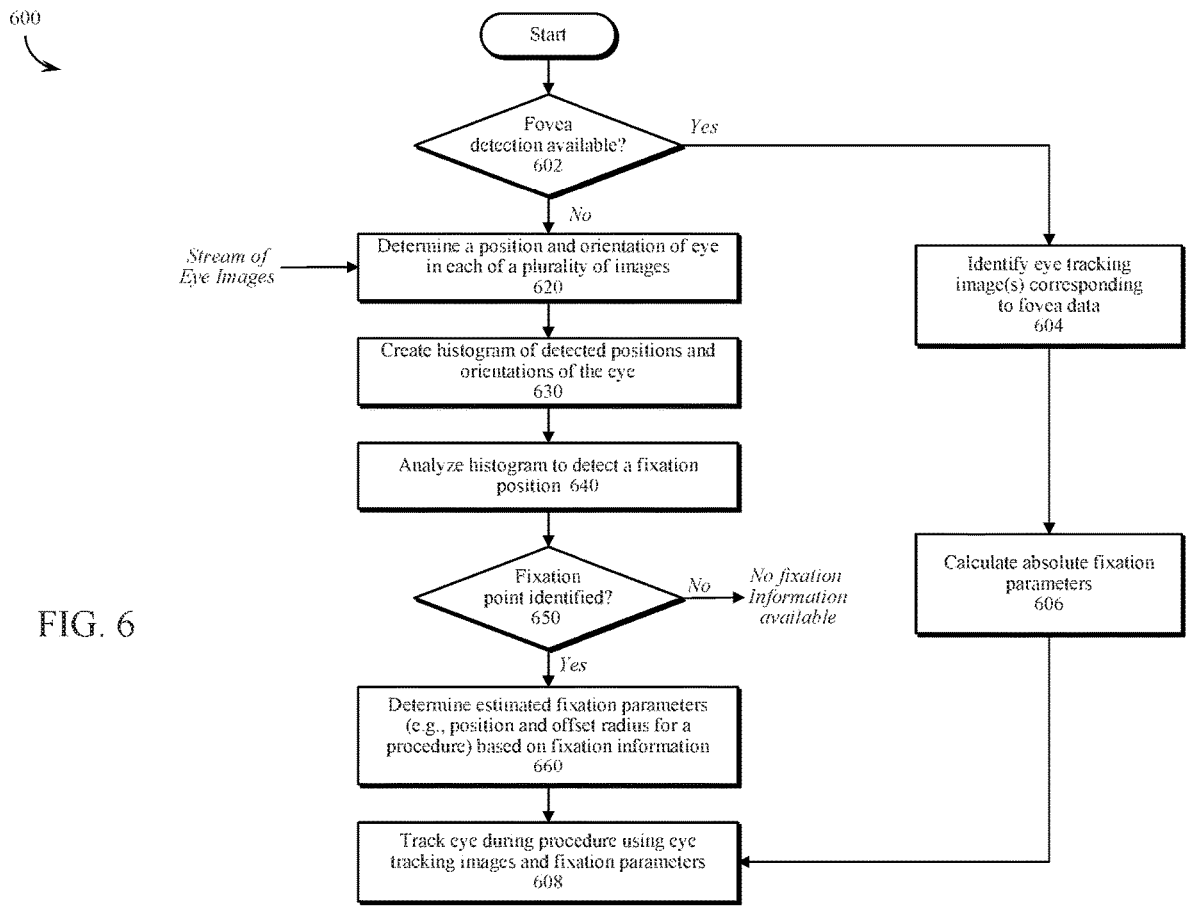
FIG. 6 illustrates a method for estimating an absolute eye position, in accordance with one or more embodiments of the present disclosure.

Referring to FIG. 6, an embodiment of a method 600 for estimating absolute eye fixation will now be described. The method 600 is performed using a computing device and an imaging system that may include a camera and an illumination system (e.g., camera 112 and illumination components 114 of FIG. 1) for imaging the surface of a patient's eye. The method determines the position and orientation of the eye by using the position of detectable features of the eye in the image (e.g., the pupil, limbus, iris features, etc.) and the position of the reflection of the illumination system at the cornea. The position of the eye is determined during a procedure or other time during which the patient is expected to be properly positioned and fixating with reference to an optical axis of the ophthalmic device. The operator may start the process by providing feedback (e.g., by pressing one or more buttons) and/or the operator may start the sequence which is then followed by the patient. Optionally, the operator may provide confirmation of the patient's compliance with the procedure.

The method 600 illustrates an embodiment for implementation by a computing device of an ophthalmic device that may include a retina OCT imaging device. To determine an absolute fixation position, the computing system determines whether fovea detection information is available (Step 602). Fovea detection information may be available, for example, if the ophthalmic device includes a retina imaging device that scanned the patient's eye while the patient was properly fixating. If fovea detection information is available, the method proceeds to step 604 where the computing system identifies eye tracking images that correspond to the detected fovea data (e.g., as described above with reference to FIGS. 1-5). In step 606, the absolute fixation parameters are calculated using the corresponding images. The patient's eye may then be tracked during a procedure using eye tracking images and the fixation parameters.

Referring back to step 602, if fovea detection is not available then the method uses the captured images of the eye (e.g., images of the surface of the eye) to estimate the absolute fixation parameters. In step 620, the computing device receives a stream of captured images from the camera and determines a position and orientation of the eye in each of a plurality of images. The computing device may process each received image or a subset of the received images (e.g., in accordance with processing constraints). The images may be received before/during a procedure and/or after a procedure when analyzing captured data.

After the position and orientation of the eye is determined for a series of captured images, a histogram is generated of the determined positions and orientations in step 630. In some embodiments, the position and orientation information include a pixel position of the center of the pupil in each of the images, which is used to construct a two-dimensional histogram of (x,y) coordinates. The position and orientation information may include an absolute position and orientation of the eye determined from each of the images, which is used to construct a two-dimensional histogram. Other representations of the position and orientation data may also be used (e.g., a heat map) in the present method. In some embodiments, operator feedback may be used to indicate images in which the patient has been instructed to fixate and/or to indicate whether the patient has not been fixating, and the corresponding images can be added to or discarded from the analysis. A procedure may be conducted in which the operator of the system instructs the patient to fixate on an object during a measurement sequence.

Figure 7:
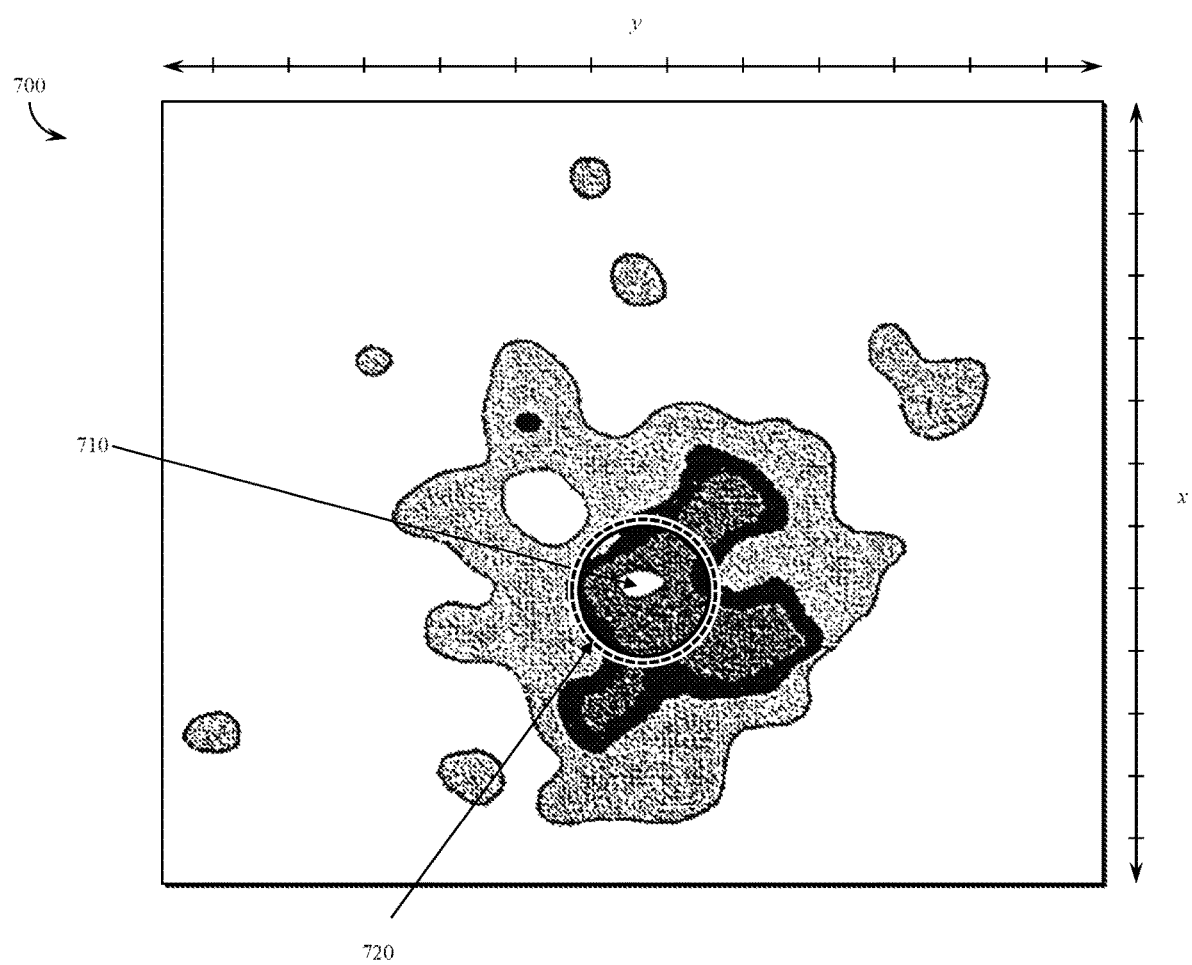
FIG. 7 illustrates an example heat map of eye position and orientation detected using an eye tracker, in accordance with one more embodiments of the present disclosure.

Referring to FIG. 7, a heat map 700 is illustrated showing an example distribution of fixation points the patient has looked at. The map may be color coded, three-dimensional, or otherwise include indicia to track the frequency in which the patient has fixated at certain spots. Other indicators (e.g., a color close to a background color) may be used to indicate a short time of fixation at that spot. In the illustrated embodiment, an area 710 of the heat map shows the most common coordinates and may indicate the position and orientation of the patient's eye while properly fixating on a target object. The dashed circle 720 indicates positions and orientations that are within a threshold offset to be chosen for a fixation determination depending on the level of precision needed for a procedure or analysis.

Figure 8:
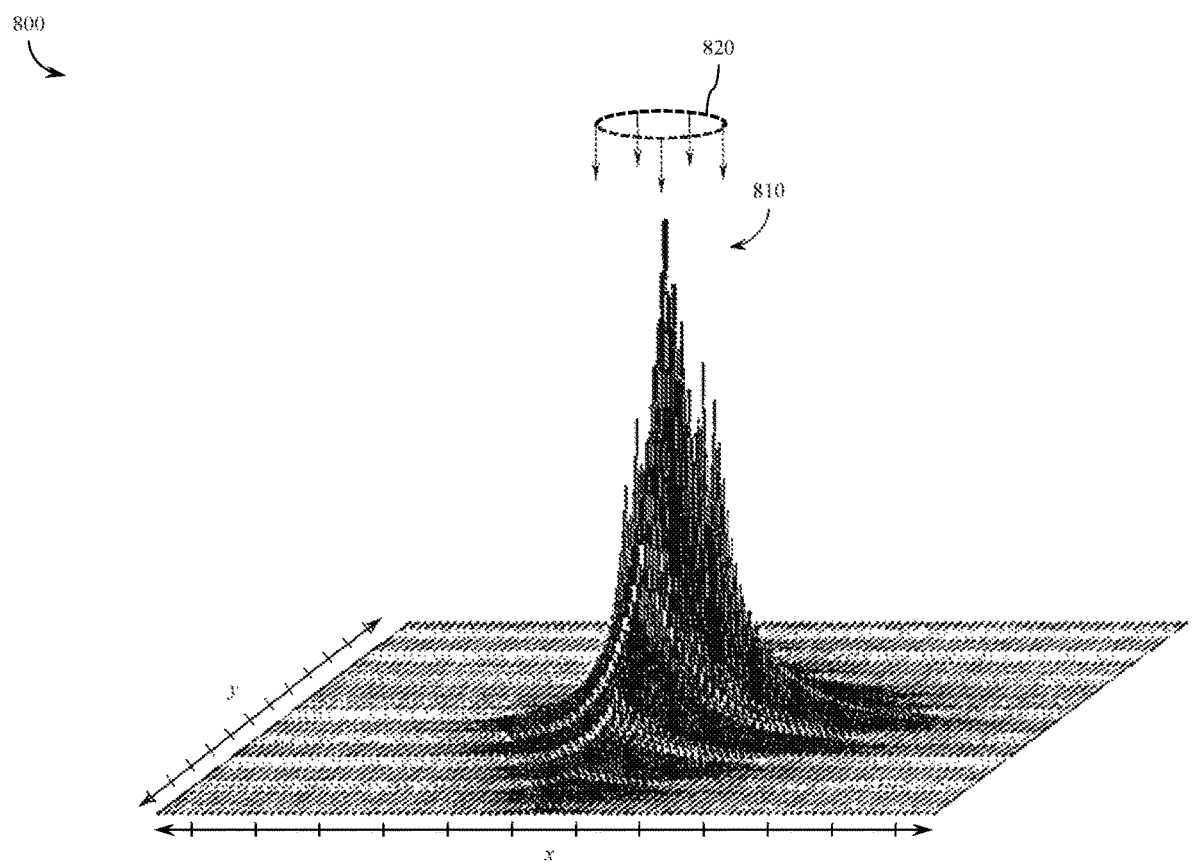
FIG. 8 illustrates an example histogram constructed of eye position and orientation data detected using an eye tracker, in accordance with one or more embodiments of the present disclosure.

FIG. 8 illustrates an example histogram 800 plotting eye coordinates detected from captured images. The maximum of this distribution 810 may be used to estimate the position and orientation of the fixated eye (e.g., by identifying the position and orientation in which the patient was most often fixating). This estimated position and orientation may be used as a reference position for further eye fixation determinations. For example, an analysis of medical data taken in a measurement sequence, may use only the data points acquired when the eye had an orientation and position within an acceptable offset (e.g., as indicated by circle 820) from the reference position (e.g., which is based at least in part on the maximum of the histogram).

As previously discussed, the histogram 800 may be constructed by plotting the fixation points determined from the captured images. For example, the histogram may track eye position as a series of pixel locations of the detected pupil or an otherwise identified center of the eye (e.g., as determined from reflections or other measurements). As the sequence of images is received and analyzed, a pattern may emerge indicating a position in which the patient is most often fixating. In some embodiments the values in the histogram may include an average of adjacent pixels and/or incorporate other smoothing.

Referring back to the method 600 of FIG. 6, in step 640 the histogram is analyzed to detect a fixation position. As previously discussed, the fixation position may relate to a maximum value of the histogram that meets certain analysis criteria. For example, a maximum may be selected based on a variety of factors including a degree of the maximum over the average value, a degree over a threshold value for a given number of images, etc. In some embodiments, the eye tracking continues during the procedure and the maximum/fixation position may be updated in real time as more images are analyzed.

Referring to step 650, if no acceptable maximum is found (or other fixation point criteria met), then eye fixation information is not available through this process. In some embodiments, the eye tracking continues during the procedure and the maximum/fixation position may be identified and/or updated in real time as more images are analyzed.

In step 660, estimated fixation parameters are determined (e.g., fixation position and offset radius acceptable for a procedure) based on the detected fixation information. The patient's eye may then be tracked during the procedure in step 608, using the eye tracking images and the estimated fixation parameters.

Figure 9:
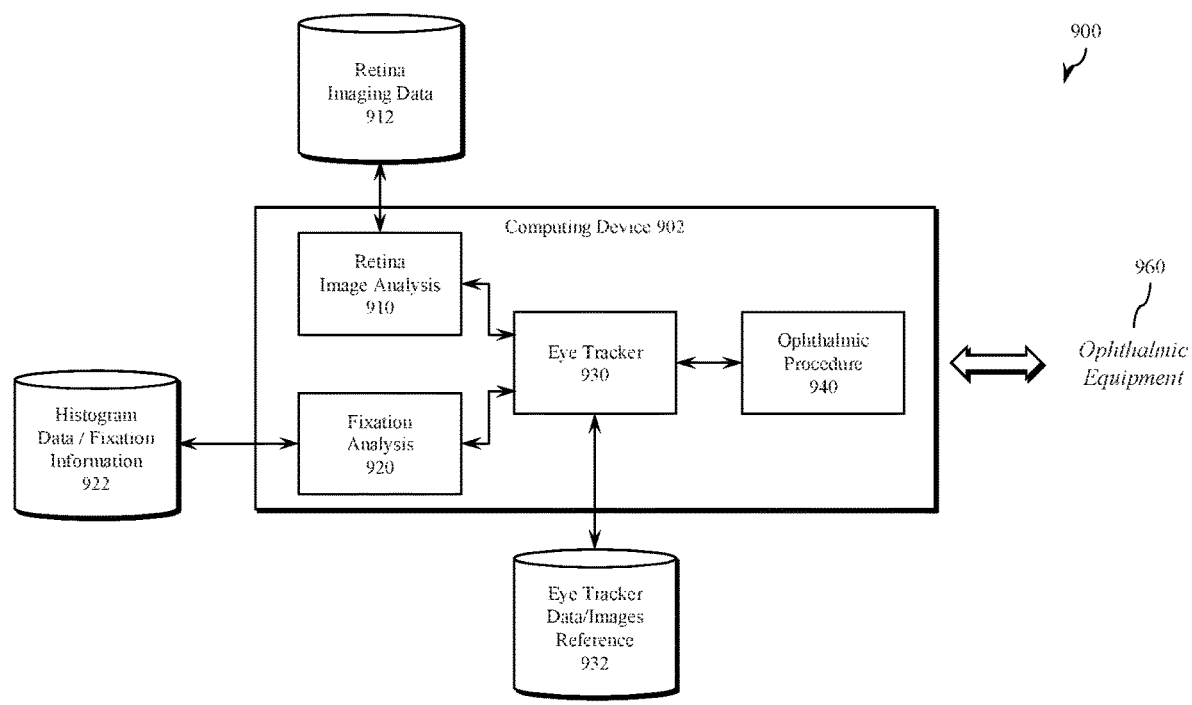
FIG. 9 illustrates an example system for implementing the method of FIG. 6, in accordance with one or more embodiments of the present disclosure.

Referring to FIG. 9, an example system 900 for implementing the method of FIGS. 6-8 will now be discussed. A computing device 902 (such as computing device 410 of FIG. 4) is communicably coupled to ophthalmic equipment 960 and is configured to perform processes associated with an eye tracker 930 and an ophthalmic procedure 940. The computing device 902 may be configured to perform a retina image analysis 910 using a retina imaging device (if available) of the ophthalmic equipment 960 and store retina image data 912. The computing device 902 further includes fixation analysis module 920, for performing an implementation of the method illustrated in FIG. 6. In one embodiment, the fixation analysis module 920 receives and analyzes a stream of eye images captured and stored (e.g., in storage 932) by the eye tracker 930, constructs and analyzes a histogram of fixation positions, and determines reference positions and associated radii. The fixation data, including histogram data, may be saved in a storage 922 (e.g., a memory or storage device).

In some embodiments, computing device 902 includes a processor that is configured to perform program instructions stored in a memory, which may include the fixation analysis module 920, the optional retina image analysis module 910, the eye tracker 930 and processes associated with the ophthalmic procedure 940.

The fixation analysis module 920 may be configured to analyze the relative gaze of a patient's eye using images captured by the eye tracker 930. The fixation analysis module 920 may construct a histogram tracking gaze orientation (e.g., pitch and yaw of the eye, relative up/down and left/right offsets, curvature/rotation, etc.) and analyze peak values of the histogram (e.g., the number of data values at each location) to get an estimate of the absolute reference. In some embodiments, the fixation analysis module 920 estimates an optical axis of the eye and an intersection with the eye tracker camera to track the gaze orientation.

The eye tracker module 930 may be configured to capture, store and process images of the patient's eye. The eye tracker module 930 may be configured to determine a patient's eye position and origination from the captured image for further analysis by the fixation analysis module 920. In some embodiments, each analyzed image may include an x,y position representative of an eye position and orientation (e.g., rotation around the x axis and y axis). The eye tracker may use information about relative orientation changes from one image to another in connection with an absolute fixation position (e.g., determined through retina image analysis 910) or estimated absolute fixation position (e.g., determined through fixation analysis module 920). In some embodiments, the fixation analysis module 920 operates on an assumption that the patient was attempting to fixate most of the time, and that the estimated absolute fixation position can be determined by constructing a histogram of x and y rotation and determining the gaze orientation that is most prominent. In various embodiments, the histogram can be constructed of pixel coordinates, rotation around x and/or y, offset values, or other data. Each image can provide a coordinate pair representing calculated eye gaze orientation which is added to the histogram.

In some embodiments, the fixation analysis module 920 is configured to analyze the histogram by detecting one distinct peak (e.g., prominent peak surrounded by smaller peaks) and determining a level of confidence that a fixation position has been detected. If no clear peak is detected, then a confidence level may be low. A radius around a detected peak may be used (e.g., humans can fixate plus/minus 0.5 degree). The threshold of peak to average and/or size of the radius may change depending on system and procedure requirements.

The computing device 902 may include one or more neural networks trained to make one or more determinations disclosed herein, including analyzing histogram data to determine whether an eye fixation position can be determined. In some embodiments, the fixation analysis may further include a comparison of known eye tracking images and/or eye fixation parameters for the patient and/or other patients. For example, one or more images may be input into a neural network trained using historical data to determine whether the eye in an image is fixating.

In various embodiments, the operator may be provided with feedback on whether the patient is or is not fixating on this axis during the data acquisition, even when the retina imaging data is not available (e.g., not part of the system and/or fovea detection not available before procedure). The systems and methods disclosed herein provide a cost-efficient solution that is suitable for use with an ophthalmic diagnostic device that uses an image capture device and an illumination system as described herein.

As will be understood by those skilled in the art, the method of the illustrated embodiment provides improved techniques for independently verifying whether the patient's eye is properly fixating on the target object during operation. By detecting the fovea at a specific point in time, the system may determine where the line of sight/visual axis is located for the patient. This information allows the system to determine whether the patient is currently fixating during a measurement sequence or other diagnostic or corrective procedure. This method combines a system that images the retina and a system that tracks the eye using surface information. From the position of the fovea in the retina image, the system can determine the eye tracking location and determine whether the eye is moving to the left or right/up or down. The system can track the user gaze, calculate an offset, determine current eye position and orientation, make determinations regarding eye fixation, determine data validity, and provide other features in accordance with the present disclosure.

Methods according to the above-described embodiments may be implemented as executable instructions that are stored on non-transitory, tangible, machine-readable media. The executable instructions, when run by one or more processors (e.g., processor 412) may cause the one or more processors to perform one or more of the processes of methods 500, 600 or other processes disclosed herein. Devices implementing methods according to these disclosures may comprise hardware, firmware, and/or software, and may take any of a variety of form factors. Typical examples of such form factors include laptops, smart phones, small form factor personal computers, personal digital assistants, and/or the like. Portions of the functionality described herein also may be embodied in peripherals and/or add-in cards. Such functionality may also be implemented on a circuit board among different chips or different processes executing in a single device, by way of further example.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A system comprising:
    an eye tracker configured to capture a first plurality of images of an eye; and
    a control processor configured to:
        detect an eye position and orientation in each of the first plurality of images;
        determine an eye fixation position and orientation relative to an optical axis of the eye tracker;
        estimate eye fixation parameters based at least in part on the determined eye fixation position and orientation;
        track the eye position and orientation by analyzing one or more images from the first plurality of images to determine the eye position and orientation relative to the eye fixation parameters; and
        detect the fixation position relative to the optical axis of the eye tracker by constructing and analyzing a histogram of detected eye positions and orientations.

2. The system of claim 1, wherein the eye fixation parameters comprise a reference position and orientation of the eye when fixated.

3. The system of claim 1, wherein analyzing the histogram further comprises determining a relative maximum value and determining whether coordinates of the relative maximum value comprise a fixation position and orientation.

4. The system of claim 3, wherein determining whether coordinates of the relative maximum value comprise a fixation position and orientation further comprise comparing the relative maximum value with a threshold and/or an average coordinate value of the histogram.

5. The system of claim 1, further comprising:
    a retina imaging system comprising an optical coherence tomography (OCT) scanner and/or a fundus camera configured to perform a retinal scan.

6. The system of claim 5, wherein the retina imaging system is configured to capture a second plurality of images of an eye;
    detect whether a fovea is present in one or more of the second plurality of images;
    identify a first image from the second plurality of images having the detected fovea;
    determine a second image from the first plurality of images having a temporal proximity to the first image; and
    analyze the second image to determine eye fixation parameters.

7. The system of claim 1, wherein the control processor is configured to track the eye position and orientation and calculate an offset from the eye fixation parameters and determine if the offset is less than a threshold value;
    wherein when the offset is less than the threshold value the eye is determined to be fixated and the control processor generates an indication of fixation; and
    wherein when the offset is greater than the threshold value the eye is determined to be out of alignment and the control processor generates an indication of no fixation.

8. The system of claim 1, wherein the control processor is further configured to perform an eye diagnostic procedure, and track eye position using the eye tracker during the eye diagnostic procedure.

9. The system of claim 1, further comprising a diagnostic device configured to perform an eye diagnostic procedure while tracking the position and orientation of the eye using an image capture device;
    wherein the diagnostic device is further configured to receive data representative of fixation and eye position during the eye diagnostic procedure based, at least in part, on the data representative of fixation and eye position.

10. A method comprising:
    capturing a first plurality of images of an eye;
    detecting an eye position and orientation in each of the first plurality of images;
    determining an eye fixation position and orientation relative to an optical axis of the eye tracker;
    estimating eye fixation parameters based at least in part on the determined eye fixation position and orientation; and
    tracking the eye position and orientation by analyzing one or more images from the first plurality of images to determine the eye position and orientation relative to the eye fixation parameters; and
    detecting the fixation position relative to the optical axis of the eye tracker, by constructing and analyzing a histogram of detected eye positions and orientations.

11. The method of claim 10, further comprising training a neural network to receive the first plurality of images and output a determination of an eye position.

12. The method of claim 10, wherein the eye fixation parameters comprise a reference position and orientation of the eye when fixated.

13. The method of claim 10, wherein analyzing the histogram further comprises determining a relative maximum value.

14. The method of claim 10, further comprising:
    performing a retina imaging scan of the eye using an optical coherence tomography (OCT) scanner.

15. The method of claim 14, further comprising:
    capturing a second plurality of images of an eye from the retina imaging scan;
    detecting whether a fovea is present in one or more of the second plurality of images;
    identifying a first image from the second plurality of images having the detected fovea;
    determining a second image from the first plurality of images having a temporal proximity to the first image; and
    analyzing the second image to determine eye fixation parameters.

16. The method of claim 10, further comprising tracking the eye position and orientation and calculating an offset from the eye fixation parameters and determine if the offset is less than a threshold value;
    wherein when the offset is less than the threshold value the eye is determined to be fixated and the control processor generates an indication of fixation; and
    wherein when the offset is greater than the threshold value the eye is determined to be out of alignment and the control processor generates an indication of no fixation.

17. The method of claim 10, further comprising performing an eye diagnostic procedure, and tracking eye position using an eye tracker during the eye diagnostic procedure.

18. The method of claim 10, further comprising performing an eye diagnostic procedure while tracking the position and orientation of the eye using an image capture device; and modifying the eye diagnostic procedure based, at least in part, on data representative of eye fixation parameters and a tracked eye position.

* * * * *